United States Patent
Maas et al.

(10) Patent No.: US 7,256,317 B2
(45) Date of Patent: Aug. 14, 2007

(54) PROCESS FOR THE PREPARATION OF SURFACTANT ALCOHOLS AND SURFACTANT ALCOHOL ETHERS, THE PREPARED PRODUCTS AND THEIR USE

(75) Inventors: Heiko Maas, Schifferstadt (DE); Michael Roeper, Wachenheim (DE); Marc Walter, Frankenthal (DE); Ralf Schulz, Speyer (DE); Juergen Tropsch, Roemerberg (DE); Hans-Ulrich Jaeger, Neustadt (DE); Peter Schwab, Bad Duerkheim (DE); Michael Schulz, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 549 days.

(21) Appl. No.: 10/765,996

(22) Filed: Jan. 29, 2004

(65) Prior Publication Data

US 2004/0186325 A1    Sep. 23, 2004

Related U.S. Application Data

(62) Division of application No. 09/868,340, filed as application No. PCT/EP99/010237 on Dec. 21, 1999, now Pat. No. 6,737,553.

(30) Foreign Application Priority Data

Dec. 23, 1998  (DE)  ................. 198 59 911

(51) Int. Cl.
C07C 27/12 (2006.01)
(52) U.S. Cl. ............... 568/694; 568/618; 568/620; 585/16; 558/31; 558/34; 558/87

(58) Field of Classification Search ........... 585/16; 536/18.6; 568/618, 620; 558/31, 34, 87
See application file for complete search history.

(56) References Cited

U.S. PATENT DOCUMENTS

| 3,448,163 A | 6/1969 | Howman et al. ........ 585/647 |
| 2005/0107628 A1* | 5/2005 | Roper et al. ........ 558/20 |

FOREIGN PATENT DOCUMENTS

| DE | 43 39 713 | 5/1995 |
| DE | 196 04 466 | 8/1997 |
| GB | 1 471 481 | 4/1977 |

* cited by examiner

*Primary Examiner*—Rosalynd Keys
(74) *Attorney, Agent, or Firm*—Oblon, Spivak, McClelland, Maier & Neustadt, P.C.

(57) ABSTRACT

The invention describes a process for the preparation of novel surfactant alcohols and surfactant alcohol ethers by derivatization of olefins having from about 10 to 20 carbon atoms or of mixtures of such olefins to give alkanols, and optional subsequent alkoxylation, which comprises subjecting a $C_4$-olefin mixture to metathesis, dimerizing the resulting olefins, and then derivatizing them to give surfactant alcohols, and optionally alkoxylating said alcohols.

The olefin mixture obtained in the dimerization has a high proportion of branched components and less than 10% by weight of compounds which contain a vinylidene group.

invention further describes the use of the surfactant alcohols and surfactant alcohol ethers to give surfactants by glycosylation or polyglycosylation, sulfation or phosphation.

11 Claims, No Drawings

PROCESS FOR THE PREPARATION OF SURFACTANT ALCOHOLS AND SURFACTANT ALCOHOL ETHERS, THE PREPARED PRODUCTS AND THEIR USE

This application is a divisional application of Application Ser. No. 09/868,340, filed Jun. 18, 2001, now U.S. Pat. No 6,737,553, which is the National Stage Application of International Application No. PCT/EP99/10237, filed Dec. 21, 1999.

The present invention relates to a process for the preparation of surfactant alcohols and surfactant alcohol ethers which, inter alia, are highly suitable as surfactants or for the preparation of surfactants. In the process, starting from $C_4$-olefin streams, olefins or olefin mixtures are prepared by a metathesis reaction which are dimerized to give an olefin mixture having from 10 to 16 carbon atoms, which comprises less than 10% by weight of compounds which have a vinylidene group, then the olefins are derivatized to give surfactant alcohols and said alcohols are optionally alkoxylated.

The invention further relates to the use of the surfactant alcohols and surfactant alcohol ethers for the preparation of surfactants by glycosylation or polyglycosylation, sulfation or phosphation.

Fatty alcohols having chain lengths from $C_8$ to $C_{18}$ are used for the preparation of nonionic surfactants. They are reacted with alkylene oxides to give the corresponding fatty alcohol ethoxylates. (Chapter 2.3 in: Kosswig/Stache, "Die Tenside" [Surfactants], Carl Hanser Verlag, Munich Vienna (1993)). The chain length of the fatty alcohol influences the various surfactant properties, such as, for example, wetting ability, foam formation, ability to dissolve grease, cleaning power.

Fatty alcohols having chain lengths from $C_8$ to $C_{18}$ can also be used for preparing anionic surfactants, such as alkyl phosphates and alkyl ether phosphates. Instead of phosphates, it is also possible to prepare the corresponding sulfates. (Chapter 2.2. in: Kosswig/Stache "Die Tenside" [Surfactants], Carl Hanser Verlag, Munich Vienna (1993))

Such fatty alcohols are obtainable from native sources, e.g. from fats and oils, or else in a synthetic manner by constructing building blocks having a lower number of carbon atoms. One variant here is the dimerization of an olefin to give a product having twice the number of carbon atoms and its functionalization to give an alcohol.

For the dimerization of olefins, a number of processes are known. For example, the reaction can be carried out over a heterogeneous cobalt oxide/carbon catalyst (DE-A-1 468 334), in the presence of acids such as sulfuric or phosphoric acid (FR 964 922), with an alkyl aluminum catalyst (WO 97/16398), or with a dissolved nickel complex catalyst (U.S. Pat. No. 4,069,273). According to the details in U.S. Pat. No. 4,069,273, the use of these nickel complex catalysts (the complexing agent used is 1,5-cyclooctadiene or 1,1,1,5,5,5-hexafluoropentane-2,4-dione) gives highly linear olefins with a high proportion of dimerization products.

Functionalization of the olefins to give alcohols with construction of the carbon skeleton about a carbon atom expediently takes place via the hydroformylation reaction, which gives a mixture of aldehydes and alcohols, which can then be hydrogenated to give alcohols. Approximately 7 million metric tons of products per annum are produced worldwide using the hydroformylation of olefins. An overview of catalysts and reaction conditions for the hydroformylation process are given, for example, by Beller et al. In Journal of Molecular Catalysis, A104 (1995), 17-85 and also in Ullmann's Encyclopedia of Industrial Chemistry, vol. A5 (1986), page 217 et seq., page 333, and the relevant literature references.

From WO 98/23566 it is known that sulfates, alkoxylates, alkoxysulfates and carboxylates of a mixture of branched alkanols (oxo alcohols) exhibit good surface activity in cold water and have good biodegradability. The alkanols in the mixture used have a chain length of greater than 8 carbon atoms, having on average from 0.7 to 3 branches. The alkanol mixture can, for example, be prepared by hydroformylation, from mixtures of branched olefins which for their part can be obtained either by skeletal isomerization or by dimerization of internal, linear olefins.

A given advantage of the process is that a $C_3$- or $C_4$-olefin stream is not used for the preparation of the dimerization feed. It follows from this that, according to the current prior art, the olefins subjected to dimerization therein must have been prepared from ethylene (e.g. SHOP process). Since ethylene is a relatively expensive starting material for surfactant manufacture, ethylene-based processes have a cost disadvantage compared with processes which start from $C_3$- and/or $C_4$-olefin streams.

Another disadvantage of this known process is the use of mixtures of internal olefins, which are only obtainable by isomerization of alpha-olefins, which is required for the preparation of branched surfactant oxo alcohols. Such processes always lead to isomer mixtures which, because of the varying physical and chemical data of the components, are more difficult to handle in terms of process engineering than pure substances. Furthermore, the additional process step of isomerization is required, by virtue of which the process has a further disadvantage. The dimerization of a pure internal olefin, such as 2-pentene or 3-hexene, and the further derivatization of the dimerization products have not been described previously.

The structure of the components of the oxo alkanol mixture depends on the type of olefin mixture which has been subjected to hydroformylation. Olefin mixtures which have been obtained by skeletal isomerization from alpha-olefin mixtures lead to alkanols which are branched predominantly at the ends of the main chain, i.e. in positions 2 and 3, calculated from the end of the chain in each case (page 56, last paragraph). Olefin mixtures which have been obtained by dimerization of olefins of shorter chain lengths give, by the process disclosed in this publication, oxo alcohols whose branches are more in the middle of the main chain and, as Table IV on page 68 shows, very predominantly on C4 and further removed carbon atoms, relative to the hydroxylcarbon atoms. By contrast, less than 25% of the branches are at the C2 and C3 positions, relative to the hydroxylcarbon atom (pages 28/29 of this document).

The surface-active end products are obtained from the alkanol mixtures either by oxidation of the —$CH_2OH$ group to give the carboxyl group, or by sulfation of the alkanols or their alkoxylates.

Similar processes for the preparation of surfactants are described in the PCT Patent Application WO 97/38957 and in EP-A-787 704. Also in the processes described therein, an alpha-olefin is dimerized to give a mixture of predominantly vinylidene-branched olefin dimers (WO 97/38957):

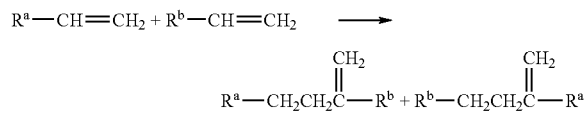

The vinylidene compounds are then double-bond-isomerized, such that the double bond migrates from the end of the chain further into the center, and are then subjected to hydroformylation to give an oxo alcohol mixture. The latter is then further reacted, e.g. by sulfation to give surfactants. A serious disadvantage of this process is that it starts from alpha-olefins. Alpha-olefins are obtained, for example, by transition-metal-catalyzed oligomerization of ethylene, Ziegler build-up reaction, wax cracking or Fischer-Tropsch processes and are therefore relatively expensive starting materials for the manufacture of surfactants. A further considerable disadvantage of this known surfactant preparation process is that a skeletal isomerization must be inserted in the process between the dimerization of the alpha-olefins and the hydroformylation of the dimerization product if predominantly branched products are desired. Because it uses a starting material which is relatively expensive for surfactant manufacture and because of the need to insert an additional process step, the isomerization, this known process is at a considerable disadvantage in terms of cost.

Surprisingly, we have now found that branched olefins and alcohols (oxo alcohols), which can be further processed to give very highly effective surfactants—referred to below as "surfactant alcohols"—, can be prepared using neither alpha-olefins nor olefins which have been prepared mainly from ethylene, but starting from cost-effective $C_4$-olefin streams, and that, furthermore, the isomerization stage can be avoided if the process is carried out according to the invention as described below. $C_4$-olefin streams are mixtures which consist essentially, preferably in an amount from greater than 80 to 85% by volume, in particular in an amount of greater than 98% by volume, of 1-butene and 2-butene, and to a lesser extent comprise, normally in an amount no more than 15 to 20% by volume, n-butane and isobutane in addition to traces of $C_5$ hydrocarbons. These hydrocarbon mixtures, referred to in the jargon also as "raffinate II", form as by-product in the cracking of high molecular weight hydrocarbons, e.g. of crude oil. While the low molecular weight olefins produced in this process, ethene and propene, are desired raw materials for the preparation of polyethylene and polypropylene, and the hydrocarbon fractions above $C_6$ are used as fuels in combustion engines and for heating purposes, it has hitherto not been possible to further process raffinate II, in particular its $C_4$-olefins, to a sufficient extent to give end products of value. The term $C_4$-olefin streams used below should therefore also encompass the gas mixture referred to as raffinate II.

The process according to the invention now opens up a method, very favorable according to the process, of processing the $C_4$-olefin streams which are produced to give surfactant alcohols of value, from which then, by various methods known per se, nonionic or anionic surfactants can be prepared.

This invention provides a process for the preparation of surfactant alcohols and surfactant alcohol ethers by derivatization of olefins having from about 10 to 20 carbon atoms or of mixtures of such olefins and optionally subsequent alkoxylation, which comprises a) subjecting a $C_4$-olefin mixture to metathesis,
b) separating off olefins having from 5 to 8 carbon atoms from the metathesis mixture,
c) subjecting the separated-off olefins individually or as a mixture to dimerization to give olefin mixtures having from 10 to 16 carbon atoms,
d) subjecting the resulting olefin mixture, optionally after fractionation, to derivatization to give a mixture of surfactant alcohols, and
e) optionally alkoxylating the surfactant alcohols.

The main features of the metathesis used in process step a) have, for example, been described in Ullmann's Encyclopedia of Industrial Chemistry, $5^{th}$ edition, volume A18, p. 235/236. Other information on carrying out the process is given for example, in K. J. Ivin, "Olefin Metathesis, Academic Press, London, (1983); Houben-Weyl, E18, 1163-1223; R. L. Banks, Discovery and Development of Olefin Disproportionation, CHEMTECH (1986), February, 112-117.

Applying the metathesis to the main constituents present in the $C_4$-olefin streams, 1-butene and 2-butene, in the presence of suitable catalysts gives olefins having from 5 to 10 carbon atoms, preferably having from 5 to 8 carbon atoms, but in particular 2-pentene and 3-hexene.

Suitable catalysts are, preferably, molybdenum, tungsten or rhenium compounds. It is particularly expedient to carry out the reaction with heterogeneous catalysis, the catalytically active metals being used in particular in conjunction with supports made from $Al_2O_3$ or $SiO_2$. Examples of such catalysts are $MoO_3$ or $WO_3$ on $SiO_2$, or $Re_2O_7$ on $Al_2O_3$.

It is particularly favorable to carry out the metathesis in the presence of a rhenium catalyst since in this case particularly mild reaction conditions are possible. Thus, the metathesis in this case can be carried out at a temperature of from 0 to 50° C. and at low pressures from about 0.1 to 0.2 MPa.

Dimerization of the olefins or olefin mixtures resulting in the metathesis step gives dimerization products which, with regard to further processing to surfactant alcohols, have a particularly favorable component and a particularly advantageous composition if a dimerization catalyst is used which contains at least one element from subgroup VIII of the Periodic Table of the Elements, and the catalyst composition and the reaction conditions are chosen such that a dimer mixture is obtained which comprises less than 10% by weight of compounds which have a structural element of the formula I (vinylidene group)

in which $A^1$ and $A^2$ are aliphatic hydrocarbon radicals.

Preference is given to using the internal, linear pentenes and hexenes present in the metathesis product for the dimerization. Particular preference is given to using 3-hexene.

The dimerization can be carried out with homogeneous or heterogeneous catalysis. Preference is given to the heterogeneous procedure since with this, on the one hand, catalyst removal is simplified, making the process more economical, and on the other hand no waste waters injurious to the environment are produced, as usually form during the removal of dissolved catalysts, for example by hydrolysis. Another advantage of the heterogeneous process is that the dimerization product does not contain halogens, in particular chlorine or fluorine. Homogeneously soluble catalysts generally contain halide-containing ligands or are used in combination with halogen-containing cocatalysts. From such catalyst systems, halogen can be incorporated into the dimerization products, which considerably adversely affects product quality and further processing, in particular hydroformylation to give surfactant alcohols.

For the heterogeneous catalysis, use is advantageously made of combinations of oxides of metals of subgroup VIII with aluminum oxide on support materials made from silicon and titanium oxides, as are known, for example, from DE-A-43 39 713. The heterogeneous catalyst can be used in a fixed bed—then preferably in coarsely particulate form as 1 to 1.5 mm chips—or in suspended form (particle size 0.05 to 0.5 mm). In the case of a heterogeneous procedure, the dimerization is advantageously carried out at temperatures of from 80 to 200° C., preferably from 100 to 180° C., at the pressure prevailing at the reaction temperature, optionally also under a protective gas at a pressure above atmospheric, in a closed system. To achieve optimal conversions, the reaction mixture is circulated several times, a certain proportion of the circulating product being continuously bled out of the system and replaced by starting material.

In the dimerization according to the invention, mixtures of monounsaturated hydrocarbons are obtained whose components predominantly have a chain length twice that of the starting olefins.

Within the scope of the details given above, the dimerization catalyst and the reaction conditions are advantageously chosen such that at least 80% of the components of the dimerization mixture have, in the range from ¼ to ¾, preferably from ⅓ to ⅔, of the chain length of their main chain, one branch, or two branches to adjacent carbon atoms.

A very characteristic feature of the olefin mixtures prepared according to the invention is their high proportion—usually greater than 75%, in particular greater than 80%— of components containing branches and the low proportion— usually below 25%, in particular below 20%— of unbranched olefins. A further characteristic is that at the branching sites of the main chain, predominantly groups having (y–4) and (y–5) carbon atoms are bonded, where y is the number of carbon atoms in the monomer used for the dimerization. The value (y–5)=0 means that no side chains are present.

In the case of $C_{12}$-olefin mixtures prepared according to the invention, the main chain preferably carries methyl or ethyl groups at the branching points.

The position of the methyl and ethyl groups on the main chain is likewise characteristic: in the case of monosubstitution, the methyl or ethyl groups are in the position P=(n/2)–m of the main chain, where n is the length of the main chain and m is the number of carbon atoms in the side groups, and in the case of disubstitution products, one substituent is in the position P and the other is on the adjacent carbon atom P+1. The proportions of monosubstitution products (a single branch) in the olefin mixture prepared according to the invention are characteristically in total in the range from 40 to 75% by weight, and the proportions of double-branched components is in the range from 5 to 25% by weight.

We have also found that the dimerization mixtures can be further derivatized particularly well when the position of the double bond satisfies certain requirements. In these advantageous olefin mixtures, the position of the double bonds relative to the branches is such that the ratio of the "aliphatic" hydrogen atoms to "olefinic" hydrogen atoms is in the range $$H_{aliph.}: H_{olefin.} = (2*n-0.5): 0.5 \text{ to } (2*n-1.9): 1.9,$$

where n is the number of carbon atoms in the olefin obtained in the dimerization.

("Aliphatic" hydrogen atoms are defined as those which are bonded to carbon atoms which are not involved in a C=C double bond (pi bond), and "olefinic" hydrocarbons are those bonded to a carbon atom which participates in a pi bond.) Particular preference is given to dimerization mixtures in which the ratio $$H_{aliph.}: H_{olefin.} = (2*n-1.0): 1 \text{ to } (2*n-1.9): 1.6.$$

The novel olefin mixtures obtainable by the process according to the invention and having the structural features given above are likewise provided by the present invention. They are useful intermediates in particular for the preparation, described below, of branched primary alcohols and surfactants, but can also be used as starting materials in other industrial processes which start from olefins, particularly when the end products are to have improved biodegradability.

If the olefin mixtures according to the invention are to be used for the preparation of surfactants, then they are firstly derivatized by processes known per se to give surfactant alcohols.

There are various methods to achieve this, which comprise either the direct or indirect addition of water (hydration) to the double bond, or an addition of CO and hydrogen (hydroformylation) to the C=C double bond.

Hydration of the olefins resulting from process step c) is expediently carried out by direct water addition with proton catalysis. An indirect route, for example via the addition of high-percentage sulfuric acid to give an alkanol sulfonate and subsequent hydrolysis to give the alkanol, is, of course, also possible. The more advantageous direct water addition is carried out in the presence of acidic, in particular heterogeneous, catalysts and generally at a very high olefin partial pressure and at very low temperatures. Suitable catalysts have proven to be, in particular, phosphoric acid on supports such as, for example, $SiO_2$ or Celite, or else acidic ion exchangers. The choice of conditions depends on the reactivity of the olefins to be reacted and can routinely be ascertained by preliminary experiments (lit.: e.g. A. J. Kresge et al. J. Am. Chem. Soc. 93, 4907 (1971); Houben-Weyl vol. 5/4(1960), pages 102-132 and 535-539). Hydration generally leads to mixtures of primary and secondary alkanols, in which the secondary alkanols predominate.

For the preparation of surfactants, it is more favorable to start from primary alkanols. It is therefore preferable to hydroformylate the derivatization of the olefin mixtures obtained from step c) by reaction with carbon monoxide and hydrogen in the presence of a suitable, preferably cobalt- or rhodium-containing, catalysts to give branched primary alcohols.

The present invention thus preferably further provides a process for the preparation of mixtures of primary alkanols which are suitable inter alia for further processing to give surfactants, by hydroformylation of olefins, which comprises using the olefin mixtures according to the invention and described above as starting material. A good overview of the process of hydroformylation with numerous other literature references can be found, for example, in the extensive article by Beller et al. in Journal of Molecular Catalysis, A104 (1995) 17-85 or in Ullmann's Encyclopedia of Industrial Chemistry, vol. A5 (1986), page 217 et seq., page 333, and the relevant literature references.

The comprehensive information given therein allows the person skilled in the art to hydroformylate even the branched olefins according to the invention. In this reaction, CO and hydrogen are added to olefinic double bonds, giving mixtures of aldehydes and alkanols according to the following reaction equation:

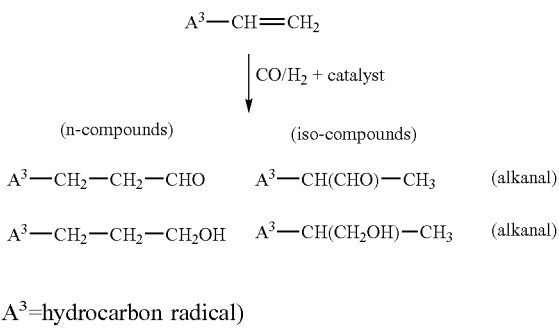

$A^3$=hydrocarbon radical)

The molar ratio of n- and iso-compounds in the reaction mixture is usually in the range from 1:1 to 20:1 depending on the hydroformylation processing conditions chosen and the catalyst used. The hydroformylation is normally carried out in the temperature range from 90 to 200° and at a $CO/H_2$ pressure of from 2.5 to 35 MPa (25 to 350 bar). The mixing ratio of carbon monoxide to hydrogen depends on whether the intention is to produce alkanals or alkanols in preference. The $CO:H_2$ ratio is advantageously from 10:1 to 1:10, preferably from 3:1 to 1:3, where, for the preparation of alkanals, the range of low hydrogen partial pressures is chosen, and for the preparation of alkanols the range of high hydrogen partial pressures is chosen, e.g. $CO:H_2=1:2$.

Suitable catalysts are mainly metal compounds of the formula $HM(CO)_4$ or $M_2(CO)_8$, where M is a metal atom, preferably a cobalt, rhodium or ruthenium atom.

Generally, under hydroformylation conditions, the catalysts or catalyst precursors used in each case form catalytically active species of the formula $H_xM_y(CO)_zL_q$, in which M is a metal of subgroup VIII, L is a ligand, which can be a phosphine, phosphite, amine, pyridine or any other donor compound, including in polymeric form, and q, x, y and z are integers depending on the valency and type of metal, and the covalence of the ligand L, where q can also be 0.

The metal M is preferably cobalt, ruthenium, rhodium, palladium, platinum, osmium or iridium and in particular cobalt, rhodium or ruthenium.

Suitable rhodium compounds or complexes are, for example rhodium(II) and rhodium(III) salts, such as rhodium(III) chloride, rhodium(III) nitrate, rhodium(III) sulfate, potassium rhodium sulfate, rhodium(II) or rhodium(III) carboxylate, rhodium(II) and rhodium(III) acetate, rhodium (III) oxide, salts of rhodium(III) acid, such as, for example, trisammonium hexachlororhodate(III). Also suitable are rhodium complexes such as rhodium biscarbonylacetylacetonate, acetylacetonatobisethylenerhodium(I). Preference is given to using rhodium biscarbonylacetylacetonate or rhodium acetate.

Suitable cobalt compounds are, for example, cobalt(II) chloride, cobalt(II) sulfate, cobalt(II) carbonate, cobalt(II) nitrate, their amine or hydrate complexes, cobalt carboxylates, such as cobalt acetate, cobalt ethylhexanoate, cobalt naphthanoate, and the cobalt caprolactamate complex. Here too it is also possible to use the carbonyl complexes of cobalt, such as dicobalt octocarbonyl, tetracobalt dodecacarbonyl and hexacobalt hexadecacarbonyl. Said compounds of cobalt, rhodium and ruthenium are known in principle and are described sufficiently in the literature, or they can be prepared by the person skilled in the art in a manner analogous to that for compounds already known.

The hydroformylation can be carried out with the addition of inert solvents or diluents or without such an addition. Suitable inert additives are, for example, acetone, methyl ethyl ketone, cyclohexanone, toluene, xylene, chlorobenzene, methylene chloride, hexane, petroleum ether, acetonitrile, and the high-boiling fractions from the hydroformylation of the dimerization products.

If the resulting hydroformylation product has too high an aldehyde content, this can be removed in a simple manner by hydrogenation, for example using hydrogen in the presence of Raney nickel or using other catalysts known for hydrogenation reactions, in particular catalysts containing copper, zinc, cobalt, nickel, molybdenum, zirconium or titanium. In the process, the aldehyde fractions are largely hydrogenated to give alkanols. A virtually residue-free removal of aldehyde contents from the reaction mixture can, if desired, be achieved by posthydrogenation, for example under particularly mild and economical conditions using an alkali metal borohydride.

The mixtures of branched primary alkanols, preparable by hydroformylation of the olefin mixtures according to the invention, are likewise provided by the present invention.

Nonionic or anionic surfactants can be prepared from the alkanols according to the invention in a different manner.

Nonionic surfactants are obtained by reaction of the alkanols with alkylene oxides (alkoxylation) of the formula II

in which $R^1$ is hydrogen or a straight-chain or branched aliphatic radical of the formula $C_nH_{2n+1}$, and n is a number from 1 to 16, preferably from 1 to 8. In particular, $R^1$ is hydrogen, methyl or ethyl.

The alkanols according to the invention can be reacted with a single alkylene oxide species or with two or more different species. The reaction of the alkanols with the alkylene oxides forms compounds which in turn carry an OH group and can therefore react afresh with one molecule of alkylene oxide. Therefore, depending on the molar ratio of alkanol to alkylene oxide, reaction products are obtained which have polyether chains of varying length. The polyether chains can contain from 1 to about 200 alkylene oxide structural groups. Preference is given to compounds whose polyether chains contain from 1 to 10 alkylene oxide structural groups.

The chains can consist of identical chain members, or they can have different alkylene oxide structural groups which differ from one another by virtue of their radical $R^1$. These various structural groups can be present within the chain in random distribution or in the form of blocks.

The reaction scheme below serves to illustrate the alkoxylation of the alkanols according to the invention using, as example, a reaction with two different alkylene oxides which are used in varying molar amounts x and y.

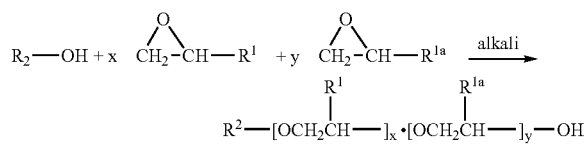

$R^1$ and $R^{1a}$ are different radicals within the scope of the definitions given for $R^1$, and $R^2$—OH is a branched alkanol according to the invention. The alkoxylation is preferably catalyzed by strong bases, which are advantageously added in the form of an alkali metal hydroxide or alkaline earth metal hydroxide, usually in an amount of from 0.1 to 1% by weight, based on the amount of the alkanol $R^2$—OH. (cf. G. Gee et al., J. Chem. Soc. (1961), p. 1345; B. Wojtech, Makromol. Chem. 66, (1966), p. 180).

Acidic catalysis of the addition reaction is also possible. As well as Bronsted acids, Lewis acids, such as, for example, $AlCl_3$ or $BF_3$, are also suitable (cf. P. H. Plesch, The Chemistry of Cationic Polymerization, Pergamon Press, New York (1963).

The addition reaction is carried out at temperatures of from about 120 to about 220° C., preferably from 140 to 160° C., in a sealed vessel. The alkylene oxide or the mixture of different alkylene oxides is introduced into the mixture of alkanol mixture according to the invention and alkali under the vapor pressure of the alkylene oxide mixture prevailing at the chosen reaction temperature. If desired, the alkylene oxide can be diluted by up to about 30 to 60% using an inert gas. This leads to additional security against explosion-like polyaddition of the alkaline oxide.

If an alkylene oxide mixture is used, then polyether chains are formed in which the various alkylene oxide building blocks are distributed in virtually random manner. Variations in the distribution of the building blocks along the polyether chain arise due to varying reaction rates of the components and can also be achieved arbitrarily by continuous introduction of an alkylene oxide mixture of a program-controlled composition. If the various alkylene oxides are reacted successively, then polyether chains having block-like distribution of the alkylene oxide building blocks are obtained.

The length of the polyether chains varies within the reaction product in a random manner about a mean, which essentially [lacuna] the stoichiometric value arising from the amount added.

The alkoxylates preparable from alkanol mixtures and olefin mixtures according to the invention are likewise provided by the present invention. They exhibit very good surface activity and can therefore be used as neutral surfactants in many areas of application.

Starting from the alkanol mixtures according to the invention, it is also possible to prepare surface-active glycosides and polyglycosides (oligoglycosides). These substances too have very good surfactant properties. They are obtained by single or multiple reaction (glycosylation, polyglycosylation) with mono-, di- or polysaccharides with the exclusion of water and with acid catalysis. Suitable acids are, for example, HCl or $H_2SO_4$. As a rule, the process produces oligoglycosides having random chain length distribution, the average degree of oligomerization being from 1 to 3 saccharide radicals.

In another standard synthesis, the saccharide is firstly acetalated with acid catalysis with a low molecular weight alkanol, e.g. butanol, to give butanol glycoside. This reaction can also be carried out with aqueous solutions of the saccharide. The lower alkanol glycoside, for example butanol glycoside, is then reacted with the alkanol mixtures according to the invention to give the desired glycosides according to the invention. After the acidic catalyst has been neutralized, excess long-chain and short-chain alkanols can be removed from the equilibrium mixture, e.g. by distillation under reduced pressure.

Another standard method proceeds via the O-acetyl compounds of saccharides. The latter are converted, using hydrogen halide preferably dissolved in glacial acetic acid, into the corresponding O-acetylhalosaccharides, which react in the presence of acid-binding agents with the alkanols to give the acetylated glycosides.

Preferred for the glycosylation of the alkanol mixtures according to the invention are monosaccharides, either hexoses, such as glucose, fructose, galactose, mannose, or pentoses, such as arabinose, xylose or ribose. Particular preference for glycosylation of the alkanol mixtures according to the invention is glucose. It is, of course, also possible to use mixtures of said saccharides for the glycosylation. Glycosides having randomly distributed sugar radicals are obtained, depending on the reaction conditions. The glycosylation can also take place several times resulting in polyglycoside chains being added to the hydroxyl groups of the alkanols. In a polyglycosylation using different saccharides, the saccharide building blocks can be randomly distributed within the chain or form blocks of the same structural groups.

Depending on the reaction temperature chosen, furanose or pyranose structures can be obtained. To improve the solubility ratios, the reaction can also be carried out in suitable solvents or diluents.

Standard processes and suitable reaction conditions have been described in various publications, for example in "Ullmann's Encyclopedia of Industrial Chemistry", 5th edition vol. A25 (1994), pages 792-793 and in the literature references given therein, by K. Igarashi, Adv. Carbohydr. Chem. Biochem. 34, (1977), pp. 243-283, by Wulff and Röhle, Angew. Chem. 86, (1974), pp. 173-187, or in Krauch and Kunz, Reaktionen der organischen Chemie [Reactions in Organic Chemistry], pp. 405-408, Hüthig, Heidelberg, (1976).

The glycosides and polyglycosides (oligoglycosides) preparable starting from alkanol mixtures and olefin mixtures according to the invention are likewise provided by the present invention.

Both the alkanol mixtures according to the invention and the polyethers prepared therefrom can be converted into anionic surfactants by esterifying (sulfating) them in a manner known per se with sulfuric acid or sulfuric acid derivatives to give acidic alkyl sulfates or alkyl ether sulfates, or with phosphoric acid or its derivatives to give acidic alkyl phosphates or alkyl ether phosphates.

Sulfating reactions of alcohols have already been described, e.g. in U.S. Pat. No. 3,462,525, 3,420,875 or 3,524,864. Details on carrying out this reaction can be found in "Ullmann's Encyclopedia of Industrial Chemistry", 5th edition vol. A25 (1994), pages 779-783 and in the literature references given therein.

If sulfuric acid itself is used for the esterification, then 75 to 100% strength by weight, preferably from 85 to 98% strength by weight, of acid is used (so-called "concentrated sulfuric acid" or "monohydrate"). The esterification can be carried out in a solvent or diluent if one is desired for controlling the reaction, e.g. the evolution of heat. In general, the alcoholic reactant is initially introduced, and the sulfating agent is gradually added with continuous mixing. If complete esterification of the alcohol component is desired, the sulfating agent and the alkanol are used in a molar ratio from 1:1 to 1:1.5, preferably from 1:1 to 1:1.2. Lesser amounts of sulfating agent can be advantageous if mixtures of alkanol alkoxylates according to the invention are used and the intention is to prepare combinations of neutral and anionic surfactants. The esterification is normally carried out at temperatures from room temperature to 85° C., preferably in the range from 45 to 75° C.

In some instances, it may be advantageous to carry out the esterification in a low-boiling water-immiscible solvent and diluent at its boiling point, the water forming during the esterification being distilled off azeotropically.

Instead of sulfuric acid of the concentration given above, for the sulfation of the alkanol mixtures according to the invention, it is also possible, for example, to use sulfur trioxide, sulfur trioxide complexes, solutions of sulfur trioxide in sulfuric acid ("oleum"), chlorosulfonic acid, sulfuryl chloride or even amidosulfuric acid.

The reaction conditions are then adapted appropriately.

If sulfur trioxide is used as sulfating agent, then the reaction can also be carried advantageously in a falling-film reactor in countercurrent, if desired also continuously.

Following esterification, the mixtures are neutralized by adding alkali and, optionally after removal of excess alkali sulfate and any solvent present, are worked up.

The acidic alkanol sulfates and alkanol ether sulfates and salts thereof obtained by sulfation of alkanols and alkanol ethers according to the invention and their mixtures are likewise provided by the present invention.

In an analogous manner, alkanols and alkanol ethers according to the invention and their mixtures can also be reacted (phosphated) to give acidic phosphoric esters. Suitable phosphating agents are mainly phosphoric acid, polyphosphoric acid and phosphorus pentoxide, but also $POCl_3$ when the remaining acid chloride functions are subsequently hydrolyzed. The phosphation of alcohols has been described, for example, in Synthesis 1985, pages 449 to 488.

The acidic alkanol phosphates and alkanol ether phosphates obtained by phosphation of alkanols and alkanol ethers according to the invention and their mixtures are also provided by the present invention.

Finally, the use of the alkanol ether mixtures, alkanol glycosides and the acidic sulfates and phosphates of the alkanol mixtures and of the alkanol ether mixtures preparable from the olefin mixtures according to the invention as surfactants is also provided by the present invention.

The working examples below illustrate the preparation and use of the surfactants according to the invention.

EXAMPLE 1

Preparation of $C_5/C_6$-olefins from $C_4$-olefin Streams by Metathesis

A butadiene-free $C_4$-fraction having a total butene content of 84.2% by weight and a molar ratio of 1-butene:2-butene of 1.06 ("raffinate II") is passed continuously, at 40° C. and 10 bar, through a tubular reactor charged with $Re_2O_7/Al_2O_3$ heterogeneous catalyst. The space velocity is adjusted to 4500 kg/(m²*h). The reactor discharge is separated by distillation and contains the following components (figures in percent by mass):

ethene: 1.15%, propene: 18.9%, butane: 15.8%, 2-butene: 19.7%, 1-butene: 13.3%, i-butene: 1.00%, 2-pentene: 19.4%, methylbutene: 0.45%, 3-hexene: 10.3%.

EXAMPLES 2A. AND 2B: HETEROGENEOUS-CATALYZED DIMERIZATION OF 3-HEXENE

2A. Fixed Bed Process

An isothermally heatable reactor having a diameter of 16 mm was filled with 100 ml of a catalyst having the following composition:

50% by weight of NiO, 34% by weight of $SiO_2$, 13% by weight of $TiO_2$, 3% by weight of $Al_2O_3$ (as in DE-A-43 39 713), conditioned for 24 hours at 160° C. in $N_2$, used as 1 to 1.5 mm chips.

5 experiments were carried out, 3-hexene (99.9% strength by weight, 0.1% by weight of $C_7$ to $C_{11}$ fractions) being passed through the fixed catalyst bed at a rate (WHSV), based on the reactor volume, of 0.25 kg/l*h, and being bled out of the system at a rate of from 24 to 28 g/h. The parameters varied in the individual experiments were the reaction temperature or the operating duration of the experiment.

Table I below shows the experimental conditions for the five experiments and the results obtained.

TABLE I

Process conditions and results in the fixed-bed process

| | Reaction conditions | | | | | |
|---|---|---|---|---|---|---|
| Temperature [° C.] | 100 | 120 | 140 | 160 | 160 | $C_{12}$ distillate |
| Pressure [bar] | 20 | 20 | 20 | 25 | 25 | |

TABLE I-continued

Process conditions and results in the fixed-bed process

| Operating hours | 12 | 19 | 36 | 60 | 107 |
|---|---|---|---|---|---|
| Liquid produced [g/h] | 24 | 27 | 27 | 28 | 27 |

Composition % by weight

| | | | | | |
|---|---|---|---|---|---|
| $C_6$ | 68.5 | 52.7 | 43.6 | 57.0 | 73.2 | 0.1 |
| $C_7$–$C_{11}$ | 0.2 | 0.2 | 0.3 | 0.2 | 0.2 | — |
| $C_{12}$ | 25.9 | 38.6 | 44.0 | 35.6 | 23.6 | 99.9 |
| >$C_{12}$ | 5.4 | 8.5 | 12.1 | 7.2 | 3.0 | — |
| Conversion | 31.4 | 47.2 | 56.4 | 42.9 | 26.7 | — |
| $C_{12}$ selectivity [% by weight] | 82.5 | 81.5 | 78.2 | 83.0 | 88.4 | — |
| S content in the liquid produced [ppm] | — | — | — | — | — | — |

The discharged product was fractionally distilled, and determination of the skeletal isomers of the $C_{12}$ fraction was carried out. Analysis revealed 14.2% by weight of n-dodecenes, 31.8% by weight of 5-methylundecenes, 29.1% by weight of 4-ethyldecenes, 6.6% by weight of 5,6-dimethyldecenes, 9.3% by weight of 4-methyl-5-ethylnonenes and 3.7% by weight of diethyloctenes.

B. Suspension Process (Fluidized Bed Process)

An isothermally heatable reactor having a diameter of 20 mm and a volume of 157 ml was filled with 30 g of a catalyst having the following composition:

50% by weight of NiO, 34% by weight of $SiO_2$, 13% by weight of $TiO_2$, 3% by weight of $Al_2O_3$ (as in DE-A-43 39 713), conditioned for 24 hours at 160° C. in $N_2$, used as 0.05 to 0.5 mm spray material.

6 experiments were carried out, 3-hexene (99.9% strength by weight, 0.1% by weight of $C_7$ to $C_{11}$ fractions) being passed through the catalyst fluidized bed from below at a rate, based on the reactor volume, of 0.25 kg/l*h. The reaction product leaving the reactor was largely recycled (recycling: feed amount varied between about 45 and 60). Parameters which were varied in the individual experiments were also the reaction temperature, the feed amount, the circulation stream, the recycle rate and the WHSV of the experiment. The experiment duration was 8 hours.

Tables 2A and 2B below show the experimental conditions for the six experiments and the results obtained.

Tables 2

Experimental conditions and results for the suspension process.

TABLE 2A

Experimental conditions

| Experiment No. | Temperature [° C.] | Pressure [bar] | Feed [g/h] | Circulation [g/h] | Recycle rate [X:1] | WHSV | Operating time [h] |
|---|---|---|---|---|---|---|---|
| 1 | 130 | 11.0 | 20 | 1200 | 60.0 | 0.127 | 8 |
| 2 | 130 | 11.0 | 23 | 1200 | 52.2 | 0.146 | 8 |
| 3 | 130 | 12.0 | 21 | 1100 | 52.4 | 0.134 | 8 |
| 4 | 130 | 12.2 | 24 | 1100 | 45.8 | 0.153 | 8 |
| 5 | 140 | 13.4 | 23 | 1180 | 51.3 | 0.146 | 8 |
| 6 | 150 | 14.1 | 22 | 1200 | 54.5 | 0.140 | 8 |

TABLE 2B

Composition of the reaction product

| Experiment No. | % $C_6$ | % > $C_6$ | % $C_{12}$ | % $C_{18}$ | % $C_{24}$ | % conversion | % $C_{12}$ selectivity |
|---|---|---|---|---|---|---|---|
| 1 | 83.9 | 0.5 | 14.3 | 1.1 | 0.2 | 16.1 | 88.82 |
| 2 | 80.5 | 0.5 | 16.9 | 1.8 | 0.3 | 19.5 | 86.67 |
| 3 | 80.3 | 0.4 | 17.0 | 1.9 | 0.3 | 19.7 | 86.29 |
| 4 | 81.6 | 0.5 | 15.5 | 2.0 | 0.3 | 18.4 | 84.24 |
| 5 | 75.9 | 0.5 | 20.4 | 2.6 | 0.5 | 24.1 | 84.65 |
| 6 | 71.1 | 0.6 | 24.0 | 3.5 | 0.7 | 28.9 | 83.04 |

The discharged product was fractionally distilled and determination of the skeletal isomers of the $C_{12}$ fraction was carried out. Analysis revealed 14% by weight of n-dodecenes, 32% by weight of 5-methylundecenes, 29% by weight of 4-ethyldecenes, 7% by weight of 5,6-dimethyldecenes, 9% by weight of 4-methyl-ethylnonenes and 4% by weight of diethyloctenes.

EXAMPLE 3

Hydroformylation of the Dodecene Mixture According to the Invention.

750 g of the dodecene mixture prepared as in Example 2B are hydroformylated with 3.0 g of $Co_2(CO)_8$ at 185° C. and 280 bar of $CO/H_2$ (volume ratio=1:1.5) with the addition of 75 g of $H_2O$ in a 2.5 l autoclave with lifter stirrer for 5 hours. Cobalt is removed oxidatively from the reaction product using 10% strength by weight acetic acid with the introduction of air at 90° C. The oxo product is hydrogenated with the addition of 10% by weight of water in a 2.5 l autoclave with lifter stirrer containing 50 g of Raney nickel at 125° C. and a hydrogen pressure of 280 bar for 10 hours. The reaction product is fractionally distilled.

450 g of a tridecanol fraction prepared in this manner are post-hydrogenated with 3.5 g of $NaBH_4$.

The OH number of the resulting tridecanol is 277 mg of KOH/g.

Using $^1$H-NMR spectroscopy, a mean degree of branching of 2.3 methyl groups/molecule was determined, corresponding to a degree of branching of 1.3.

EXAMPLE 3A

Hydroformylation of a Dodecene Mixture According to the Invention 2.12 kg of the dodecene mixture prepared as in Example 2A are hydroformylated with 8 g of $CO_2(CO)_8$ at 185° C. and 280 bar of $CO/H_2$ (volume ratio 1:1) with the addition of 210 g of water in a 5 l rotary-stirrer autoclave for 5 hours. Cobalt is removed oxidatively from the reaction product using 10% strength by weight acetic acid with the introduction of air at 90° C. The resulting oxo product is hydrogenated in a 5 l tubular reactor in trickle mode over a Co/Mo fixed bed catalyst at 175° C. and a hydrogen pressure of 280 bar with the addition of 10% by weight of water. The alcohol mixture is worked up by distillation. The resulting tridecanol has an OH number of 279 mg of KOH/g; using $^1$H-NMR spectroscopy, a mean degree of branching of 1.53 is measured.

EXAMPLE 3B

Hydroformylation of a Dodecene Mixture According to the Invention.

50 mg of rhodium biscarbonylacetylacetonate, 4.5 g of a polyethyleneimine of molar mass $M_W$=460,000, in which 60% of all nitrogen atoms have been acylated with lauric acid, 800 g of a dodecene mixture prepared as in Example 2A and 196 g of toluene are heated to 150° C. in a 2.5 l autoclave with lifter stirrer under a pressure of 280 bar of $CO/H_2$ (volume ratio 1:1) for 7 hours. The autoclave is then cooled, decompressed and emptied. Analysis of the resulting reaction product by gas chromatography reveals an olefin conversion of 93%. The resulting oxo product is hydrogenated in a 2.5 l tubular reactor in trickle mode over a Co/Mo fixed bed catalyst at 175° C. and a hydrogen pressure of 280 bar with the addition of 10% by weight of water, and the resulting alcohol mixture is worked up by distillation. The resulting tridecanol has a OH number of 279 mg of KOH/g; using $^1$H-NMR spectroscopy, a mean degree of branching of 1.63 is measured.

EXAMPLE 3C

Hydroformylation of a Dodecene Mixture According to the Invention.

50 mg of rhodium biscarbonylacetylacetonate, 4.5 g of a polyethyleneimine of molar mass $M_W$=460,000, in which 60% of all nitrogen atoms have been acylated with lauric acid, 800 g of a dodecene mixture prepared as in Example 2A and 196 g of toluene are heated to 160° C. in a 2.5 l autoclave with lifter stirrer under a pressure of 280 bar of $CO/H_2$ (volume ratio 1:1) for 7 hours. The autoclave is then cooled, decompressed and emptied. Analysis of the resulting reaction product by gas chromatography reveals an olefin conversion of 94%. The resulting oxo product is hydrogenated in a 2.5 l tubular reactor in trickle mode over a Co/Mo fixed bed catalyst at 175° C. and a hydrogen pressure of 280 bar with the addition of 10% by weight of water, and the resulting alcohol mixture is worked up by distillation. The resulting tridecanol has a OH number of 279 mg of KOH/g; using $^1$H-NMR spectroscopy, a mean degree of branching of 1.69 is measured.

EXAMPLES 4A AND 4B

Preparation of Fatty Alcohol Ethoxylates

A. Fatty Alcohol Ethoxylate Containing 7 mol of Ethylene Oxide.

400 g of the alkanol mixture prepared as in Example 3 are introduced with 1.5 g of NaOH into a dry 2 l autoclave. The autoclave contents are heated to 150° C., and 616 g of ethylene oxide are forced into the autoclave under pressure. After all of the ethylene oxide has been introduced into the autoclave, the autoclave is maintained at 150° C. for 30 minutes. Following cooling, the catalyst is neutralized by adding sulfuric acid.

The resulting ethoxylate is a neutral surfactant. It has a cloud point of 72° C., measured in accordance with DIN 53917, 1% strength by weight in 10% strength by weight aqueous butyldiglycol solution. The surface tension of a solution of 1 g/l of the substance in water is 27.3 mN/m, measured in accordance with DIN 53914.

B. Fatty Alcohol Ethoxylate Containing 3 mol of Ethylene Oxide.

600 g of the alkanol mixture prepared as in Example 3B are introduced with 1.5 g of NaOH into a dry 2 l autoclave. The autoclave contents are heated to 150° C., and 396 g of ethylene oxide are forced into the autoclave under pressure. After all of the ethylene oxide has been introduced into the autoclave, the autoclave is maintained at 150° C. for 30 minutes. Following cooling, the catalyst is neutralized by adding sulfuric acid.

The resulting ethoxylate is a neutral surfactant. It has a cloud point of 43.5° C., measured in accordance with DIN 53917, 1% strength by weight in 10% strength by weight aqueous butyldiglycol solution. The surface tension of a solution of 1 g/l of the substance in water is 26.1 mN/m, measured in accordance with DIN 53914.

EXAMPLES 5A AND 5B

Preparation of Alkyl and Alkyl Ether Phosphates

A. Alkyl Phosphate.

300 g of the alcohol mixture prepared as in Example 3B are heated to 60° C. in a stirred vessel under nitrogen, and 125 g of polyphosphoric acid are added slowly thereto. During the addition, the temperature must not exceed 65° C. Toward the end of the addition, the mixture is heated to 70° C. and further stirred at this temperature for 1 hour.

The resulting product is an anionic surfactant. An aqueous solution of the substance in water has, at a concentration of 1 g/l, a surface tension of 29.8 mN/m, measured in accordance with DIN 53914.

B. Alkyl Ether Phosphate.

560 g of the fatty alcohol ethoxylate mixture prepared as in Example 4B are heated to 60° C. in a stirred vessel under nitrogen, and 92 g of polyphosphoric acid are added slowly thereto. During the addition, the temperature must not exceed 65° C. Toward the end of the addition, the mixture is heated to 70° C. and further stirred at this temperature for 1 hour.

The resulting product is an anionic surfactant. An aqueous solution of the substance in water has, at a concentration of 1 g/l, a surface tension of 37.7 mN/m, measured in accordance with DIN 53914.

We claim:

1. A novel olefin mixture preparable by the following steps,
   subjecting a $C_4$-olefin mixture to metathesis,
   separating off olefins having from 5 to 8 carbon atoms from the metathesis mixture,
   subjecting the separated-off olefins individually or as a mixture to dimerization to give olefin mixtures having from 10 to 16 carbon atoms,
   wherein
   a) the components have from 10 to 16 carbon atoms
   b) the proportion of unbranched olefins is less than 25% by weight
   c) the proportion of components having a structural element of the formula I (vinylidene group)

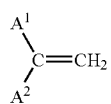

(I)

wherein A1 and A2 represent aliphatic hydrocarbon groups, is below 10% by weight.

2. An olefin mixture as claimed in claim 1, which has a proportion of unbranched olefins of less than 20% by weight.

3. An olefin mixture as claimed in claim 1, wherein at least 80% of the components of the dimerization mixture have, in the range from ¼ to ¾, of the chain length of their main chain, one branch, or two branches to adjacent carbon atoms.

4. An olefin mixture as claimed in claim 1, wherein, at the branching sites of the main chain, predominantly groups having (y-4) and (y-5) carbon atoms are bonded, where y is the number of carbon atoms in the monomer used for the dimerization.

5. An olefin mixture as claimed in claim 1, wherein the ratio of aliphatic to olefinic hydrogen atoms is in the range
$H_{aliph.}:H_{olefin.}=(2*n-0.5):0.5$ to $(2*n-1.9):1.9$, where n is the number of carbon atoms in the olefin obtained in the dimerization.

6. An olefin mixture as claimed in claim 1, wherein the ratio of aliphatic to olefinic hydrogen atoms is in the range
$H_{aliph.}:H_{olefin.}=(2*n-1.0):1$ to $(2*n-1.6):1.6$.

7. A novel surfactant alcohol obtainable by the following steps
   subjecting a $C_4$-olefin mixture to metathesis;
   separating off olefins having from 5 to 8 carbon atoms from the metathesis mixture;
   subjecting the separated-off olefins individually or as a mixture to dimerization to give olefin mixtures having from 10 to 16 carbon atoms;
   subjecting the resulting olefin mixture, optionally after fractionation, to derivatization to give a mixture of surfactant alcohols; and optionally
   alkoxylating the surfactant alcohols; wherein the novel surfactant
   a) has 11 to 17 carbon atoms and
   b) comprises a proportion of unbranched alcohols of below 25% by weight, and its alkoxylation products.

8. A method for the preparation of surfactants comprising chemically modifying the surfactant alcohol of claim 7.

9. A method according to claim 8, comprising:
   esterification of said surfactant alcohol with sulfuric acid or sulfuric acid derivatives to give acidic alkyl sulfates or alkyl ether sulfates.

10. A method according to claim 8, comprising esterification of said surfactant alcohol with phosphoric acid or its derivatives to give acidic alkyl phosphates or alkyl ether phosphates.

11. An olefin mixture as claimed in claim 1, wherein at least 80% of the components of the dimerization mixture have, in the range from ⅓ to ⅔, of the chain length of their main chain, one branch, or two branches to adjacent carbon atoms.

* * * * *